(12) United States Patent
Kürkure

(10) Patent No.: US 7,517,086 B1
(45) Date of Patent: Apr. 14, 2009

(54) COMPENSATING FOR DEFECTS IN HUMAN VISION WHILE DISPLAYING TEXT AND COMPUTER GRAPHICS OBJECTS ON A COMPUTER OUTPUT DEVICE

(75) Inventor: Uday Kürkure, Los Altos Hills, CA (US)

(73) Assignee: Adobe Systems Incorporated, San Jose, CA (US)

( * ) Notice: Subject to any disclaimer, the term of this patent is extended or adjusted under 35 U.S.C. 154(b) by 0 days.

(21) Appl. No.: 11/377,717

(22) Filed: Mar. 16, 2006

(51) Int. Cl.
*A61B 3/00* (2006.01)
(52) U.S. Cl. ..................................... 351/246
(58) Field of Classification Search ................ 351/246, 351/223, 239, 241
See application file for complete search history.

(56) References Cited

U.S. PATENT DOCUMENTS

| | | | |
|---|---|---|---|
| 5,233,333 A | 8/1993 | Borsuk | |
| 5,475,399 A | 12/1995 | Borsuk | |
| 5,513,342 A | 4/1996 | Leong | |
| 6,954,897 B1 | 10/2005 | Noguchi | |
| 6,968,502 B1 | 11/2005 | Kuhomura | |
| 7,272,258 B2 * | 9/2007 | Berkner et al. | 382/176 |
| 2005/0106537 A1 | 5/2005 | Chepaitis | |
| 2005/0193337 A1 | 9/2005 | Noguchi et al. | |
| 2005/0206656 A1 | 9/2005 | Cooper | |
| 2006/0023163 A1 * | 2/2006 | Foster | 351/246 |
| 2006/0280338 A1 | 12/2006 | Rabb | |

\* cited by examiner

*Primary Examiner*—Alicia M Harrington
(74) *Attorney, Agent, or Firm*—Robert C. Kowert; Meyertons, Hood, Kivlin, Kowert & Goetzel, P.C.

(57) ABSTRACT

One embodiment of the present invention provides a system that facilitates selecting a magnification scale factor based on an optometric prescription. The system operates by receiving an optometric prescription from a user. Next, the system selects the magnification scale factor for an output based on the user's optometric prescription, and renders the text and other graphics objects with the selected magnification so that the document becomes legible to the user with or without corrective lenses. Finally, the system displays the scaled output.

20 Claims, 4 Drawing Sheets

NEAR VISION CHART 200

| | DISTANCE CORRELATION | JAEGER | POINT SIZE | VISUAL EFFICIENCY % |
|---|---|---|---|---|
| D T 4 | 20/800 | | 72 | 5% |
| L E S 3 | 20/400 | | 42 | 10% |
| R F X B N | 20/250 | 18 | 30 | 15% |
| P O 5 7 A | 20/200 | 16 | 26 | 20% |
| 9 V M C L | 20/100 | 10 | 14 | 50% |
| K S 3 Z 7 | 20/70 | 7 | 10 | 65% |
| N R E T X | 20/50 | 5 | 8 | 75% |
| O R D F M P | 20/40 | 3 | 6 | 85% |
| V J F X G H | 20/30 | 2 | 5 | 90% |
| P J S E A R | 20/20 | 1 | 4 | 100% |

This card has been specially designed for the vision care practitioner to aid in standardized measurements of near point acuity. This card should be held at approximately 16 inches away from the patients face under standard room illumination.

FIG. 2

COMPENSATING FOR DEFECTS IN HUMAN VISION WHILE DISPLAYING TEXT AND COMPUTER GRAPHICS OBJECTS ON A COMPUTER OUTPUT DEVICE

BACKGROUND

1. Field of the Invention

The present invention relates to mechanisms for displaying text and other computer graphics objects, such as images and line art. More specifically, the present invention provides a method and an apparatus for displaying text and other computer graphics objects in a manner that compensates for defects in a human eye.

2. Related Art

As people age, they tend to suffer from presbyopia, or the inability to focus on objects close up, and typically cannot read cell phone displays and computer displays without taking off their corrective lenses. Moreover, people who generally suffer from hyperopia, or farsightedness, have a difficult time reading cell phone displays or computer displays without the aid of corrective lenses.

Constantly putting on and removing eyeglasses or other corrective lenses can be very annoying. Moreover, sometimes people do not have the time to do so when reading a cell phone or computer display. For example, consider the case where a farsighted person with presbyopia receives a call on a cell phone while her glasses are in her handbag. By the time she is able to retrieve her glasses and put them on to see the caller ID of the incoming call, the caller might have already been routed to voicemail. Conversely, if a nearsighted person with presbyopia receives a call while driving, it may not be feasible for her to remove her glasses while driving to view the information on the display.

To remedy this problem, many people set the magnification scale factor for the displays on their computer systems and cell phones to a very large setting. While this helps nearsighted individuals with presbyopia to see these displays with their glasses on, and farsighted individuals with presbyopia to see these displays with their glasses off, it consumes a large area of the display and effectively reduces the amount of information that can be displayed at a given time.

Hence, what is needed is a method to assist people that have vision problems when viewing computer system and cell phone displays while minimizing the problems listed above.

SUMMARY

One embodiment of the present invention provides a system that facilitates selecting a magnification scale factor based on an optometric prescription. The system operates by receiving an optometric prescription from a user. Next, the system selects the magnification scale factor for an output based on the user's optometric prescription, and renders the text and other graphics objects with the selected magnification so that the document becomes legible to the user with or without corrective lenses. Finally, the system displays the scaled output.

In a variation on this embodiment, receiving the optometric prescription involves determining the optometric prescription. This involves presenting an eye chart to the user, and then receiving a selection of a smallest legible line on the eye chart from the user. Next, the system determines the optometric prescription from the selected legible line.

In a variation on this embodiment, displaying the scaled output can include displaying the scaled output on a CRT or LCD display, or printing the scaled output.

In a variation on this embodiment, the optometric prescription is specified as diopters.

In a variation on this embodiment, the optometric prescription is specified as a distance correlation.

In a variation on this embodiment, the optometric prescription is specified as a Jaeger Number.

In a variation on this embodiment, the optometric prescription is specified as a font point size.

In a variation on this embodiment, the optometric prescription is specified as a visual efficiency percentage.

BRIEF DESCRIPTION OF THE FIGURES

FIG. 2 illustrates a near-vision chart in accordance with an embodiment of the present invention.

DETAILED DESCRIPTION

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the claims.

The data structures and code described in this detailed description are typically stored on a computer-readable storage medium, which may be any device or medium that can store code and/or data for use by a computer system. This includes, but is not limited to, magnetic and optical storage devices such as disk drives, magnetic tape, CDs (compact discs), DVDs (digital versatile discs or digital video discs), or any device capable of storing data usable by a computer system.

Overview

Figure 1:
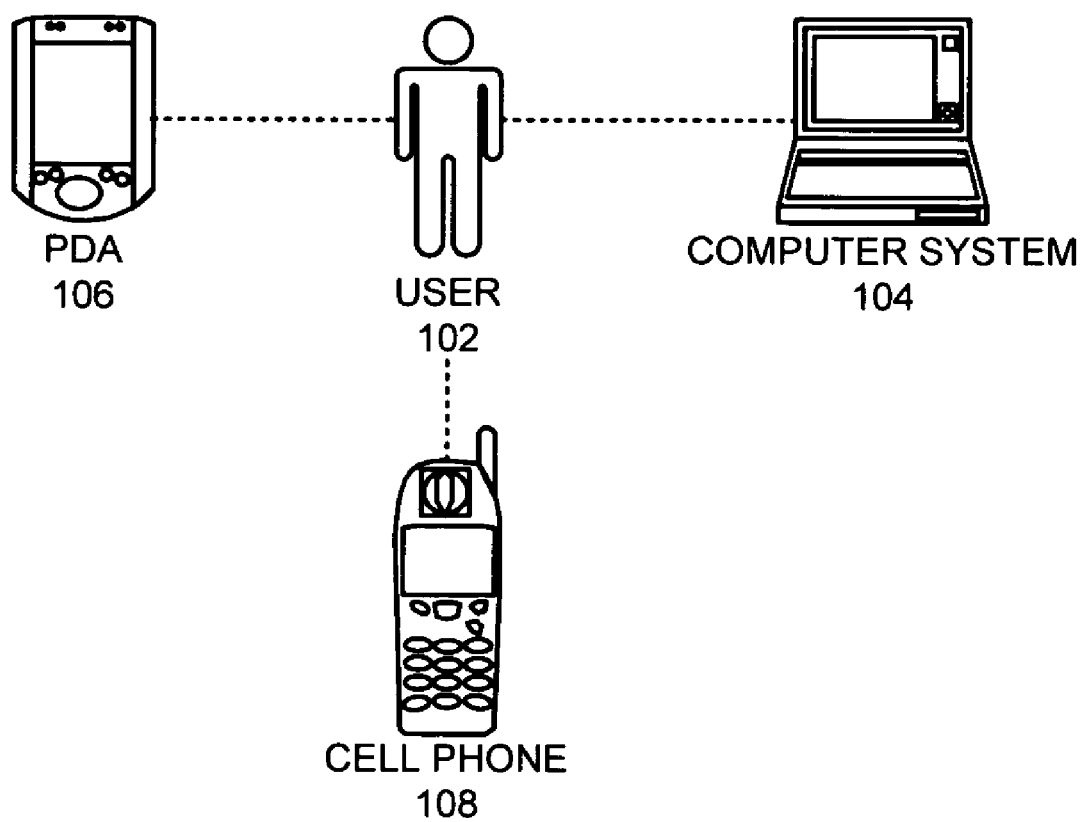
FIG. 1 illustrates an assortment of computing devices in accordance with an embodiment of the present invention.

FIG. 1 illustrates an assortment of computing devices in accordance with an embodiment of the present invention. FIG. 1 includes user 102, computer system 104, Personal Digital Assistant (PDA) 106, and cell phone 108. Note that computer system 104 can generally include any type of computer system, including, but not limited to, a computer system based on a microprocessor, a mainframe computer, a digital signal processor, a portable computing device, a personal organizer, a device controller, and a computational engine within an appliance. One embodiment of the present invention provides a system that facilitates setting a magnification scale factor for a computing device, such as computer system 104, based on a user's optometric prescription. In this embodiment, the user 102 specifies the user's optometric prescription, and the system determines the smallest font that the user 102 should be able to read with or without corrective lenses. Then computer system 104 automatically renders text and other objects based on the user's optometric prescription.

In one embodiment of the present invention, the optometric prescription is specified in diopters. A user 102 may enter her optometric prescription as specified on her prescription form from her optometrist. For example, a user 102 might enter a "+1.75" diopter spherical correction for her left eye, and a "+2.0" diopter spherical correction for her right eye. The computer system 104 then determines the appropriate magnification scale factor for a user with this prescription.

In another embodiment of the present invention, the optometric prescription is specified in a standard distance correlation. For example, a user 102 may enter a distance correlation of "20/100." These numbers represent the distance that the user 102 can read a line of text compared to the distance required by someone with normal vision. In the example above, the user 102 can read an item of text at a distance of 20 feet that a user with normal vision could read at 100 feet. Likewise, a user with normal vision would have a distance correlation of "20/20," and would require no correction. This distance correlation is well known to those skilled in the art.

In one embodiment of the present invention, the optometric prescription is specified in various other factors, such as a visual efficiency percentage, a font point size, and a Jaeger number. In fact, any quantifiable means for measuring the visual efficiency of a user may be used. In one embodiment of the present invention, the system maintains a "mapping table" of associations between various measurement types. For example, the table might include a distance correlation of "20/70" that is equivalent to a Jaeger number of "7" and a "10" point font size.

In one embodiment of the present invention, the computer system 104 adjusts the magnification scale factor for the printed material to ensure that the printed material is legible to the user 102 with or without corrective lenses.

In one embodiment of the present invention, a user 102 is presented with a chart including text of various font sizes. The user 102 is then asked to select the smallest font that is legible with and without corrective lenses. The computer system 104 can then use this selection to adjust the magnification scale factor accordingly.

FIG. 2 illustrates a near-vision chart 200 in accordance with an embodiment of the present invention. Many visual acuity charts are designed such that the letter sizes on each line follow a geometric progression. The letter sizes change approximately by 1.25 times between lines. Typically, there are two types of charts: far vision chart and near vision chart. The eye prescription of an individual is determined by having the individual read the visual acuity charts with the naked eye. In the embodiment illustrated in FIG. 2, each line on the near vision chart 200 has letters with different point sizes. Each line also includes a visual efficiency percentage, a Jaeger number (except for the top two lines), a point size and a distance correlation, such as "20/20."

For example, as illustrated, if a person has 100% visual efficiency, he or she can read letters sized to 4 points at a distance of 16 inches. This person's near vision has a Jaeger number of 1. In contrast, if a person has 65% visual efficiency, he or she can read 10 letters that are 10 points in size. This person's near vision has a Jaeger number of 7.

Alternatively, near vision prescriptions obtained from an optometrist are typically specified in diopters. Lenses with positive diopter rating are magnifying lenses. For example, a "+3.0" diopter lens will magnify an object 1.75 times depending on the viewing distance.

In one embodiment of the present invention, an application displaying the document will consult the prescription of the user 102 and most frequent point size in the document, and then magnify the document accordingly. For example, the application displaying a 4 point document for person with 65% near vision efficiency will magnify the document at 250% so that it becomes a 10 point document on the display and the person can read it without correcting glasses. Once the magnification factor is determined, the application uses a transformation matrix to render the output for the user 102. This transformation matrix is described in detail below. In a variation on this embodiment, the application displaying the document will consult the prescription of the user 102 and the minimum point size in the document, and then magnify the document accordingly.

In one embodiment of the present invention, an application displaying the document will consult the prescription of the user 102 and most frequent point size in the document, and then reduce the magnification scale of the document accordingly.

For example, in case of Adobe® Acrobat®, the distiller can record the most frequently used point size and font per page in the PDF file. Acrobat® Reader® can then consult a user 102's prescription, most frequently used point size, and font, and can then determine the default magnification scale factor per page for the document to be displayed. In one embodiment of the present invention, the default scale factor is determined based on fonts used, letter sizes and user's eye prescription. Note that the font type is used in determining the magnification scale factor because different fonts appear to have different sizes for the same point specification. For example, an 8-point Arial font looks similar in size to a 9-point Times Roman font.

Based on the example above, in one embodiment of the present invention, Adobe® Acrobat® Reader® derives a scaling factor "S" that makes text readable for user 102 with or without corrective lenses. Adobe® Acrobat® and Postscript® then uses the Adobe® Graphics Model two dimensional transformation matrix. This transformation matrix is used to achieve translation, rotation and scaling. The new transformation matrix is the multiplication of [Sx 0 0, 0 Sy 0, 0 0 1] and the original transformation matrix [a b 0, c d 0, tx ty 1]. The rendering of all the objects in the page is based on the new transformation matrix. Acrobat® Reader® invokes the Adobe® Graphics model Application Programming Interfaces (APIs) with the new transformation matrix to render the output. The existing functions in Adobe®'s Graphics Model make this very easy to implement.

In one embodiment of the present invention, user 102 can have different profiles for each device, as well as multiple profiles on each device. For example, user 102 may have a profile on cell phone 108 that user 102 uses without corrective lenses. In addition, user 102 may also have a separate profile on cell phone 108 that user 102 uses with the aid of corrective lenses. Being able to switch between multiple profiles can potentially save user 102 quite a bit of time and difficulty in switching the display settings for user 102's current condition (with or without corrective lenses).

Process of Rendering a Display Output for Optometric Prescriptions

Figure 3:
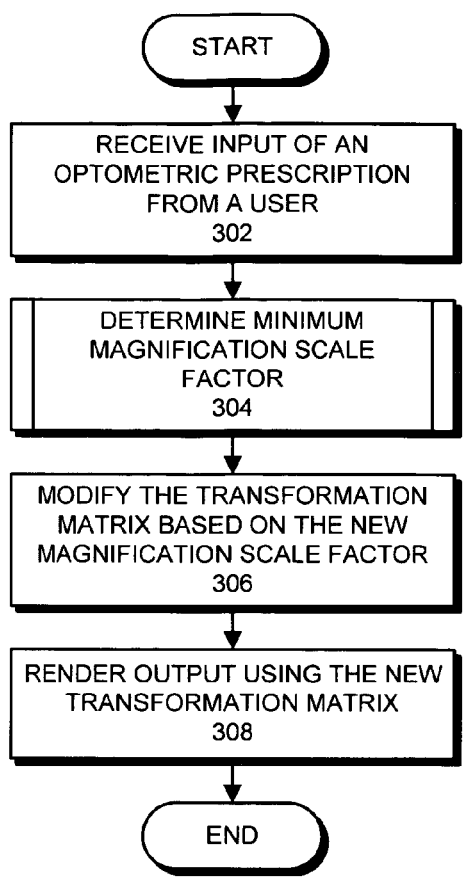
FIG. 3 presents a flow chart illustrating the process of rendering a display output for an optometric prescription in accordance with an embodiment of the present invention.

FIG. 3 presents a flow chart illustrating the process of rendering a display output for an optometric prescription in accordance with an embodiment of the present invention. The system starts by receiving an input of an optometric prescription from a user (step 302). As described previously, the optometric prescription can be specified in diopters, as a distance correlation, as a Jaeger number, as a point size, as a visual efficiency, or as any other quantifiable means.

Next, the system determines the minimum possible magnification scale factor for near-vision that is legible to the user with or without corrective lenses (step 304). This step is described in more detail in the description for FIG. 5. Note that it may be necessary for the system to choose between two different magnification scale factors if the optometric prescription for the user is vastly different for each eye. In this case, the system may be configured to choose the larger magnification scale factor, the smaller magnification scale factor, or a magnification scale factor in between the two magnification scale factors.

The system then modifies the transformation matrix based on the magnification scale factor (step 306). Modifying the transformation matrix facilitates in rendering the scaled output for user 102, as described previously.

Finally, the system renders the display output using the modified transformation matrix (step 308). Note that rendering the display output can include rendering the display output for display on a CRT or an LCD, or rendering display output to a printer for printing.

Determining an Optometric Prescription

Figure 4:
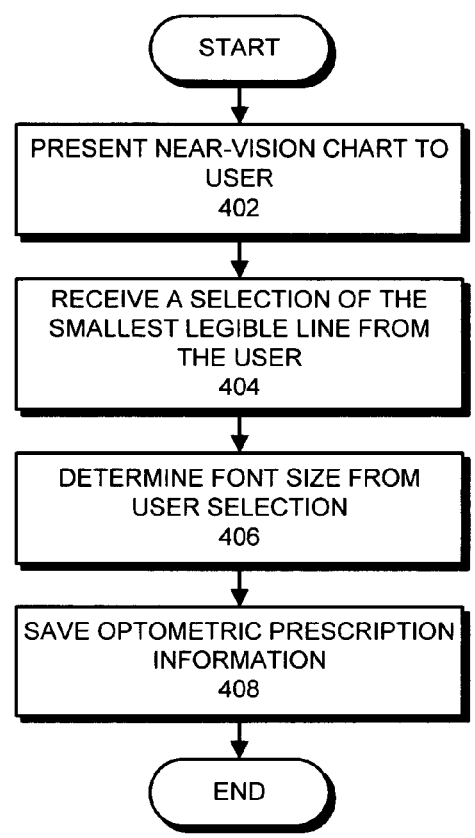
FIG. 4 presents a flow chart illustrating the process of determining an optometric prescription in accordance with an embodiment of the present invention.

FIG. 4 presents a flow chart illustrating the process of determining an optometric prescription in accordance with an embodiment of the present invention. The system starts by presenting a near-vision chart to a user (step 402). Next, the system receives from the user a selection of the smallest legible line (step 404). The system then determines the magnification scale factor from the user selection (step 406). Note that this can include using the size of the font selected, or may include increasing the font slightly from the size selected to account for variations in the representations of different fonts. This can also include adjusting the magnification scale factor to account for variations in different fonts.

Determining a Minimum Magnification Scale Factor

Figure 5:
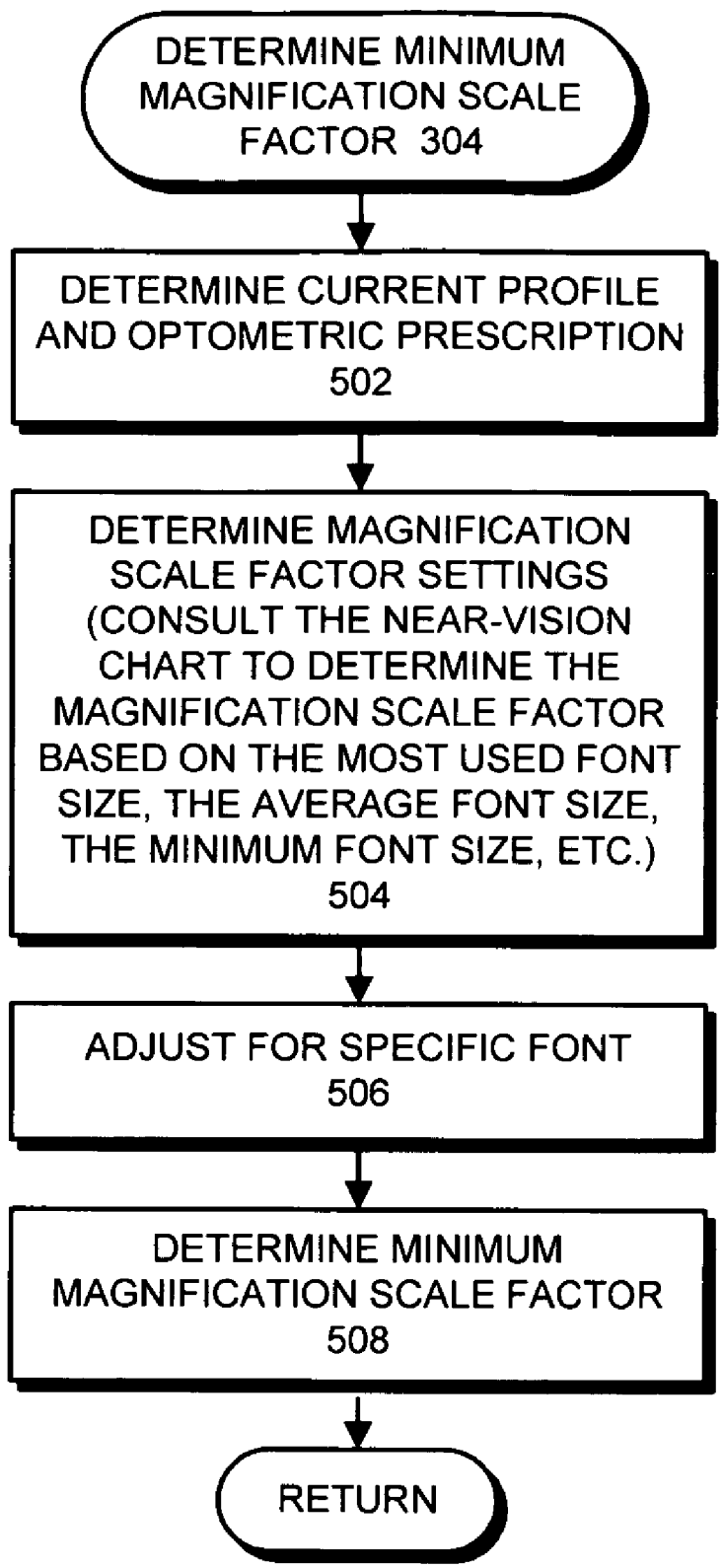
FIG. 5 presents a flow chart illustrating the process of determining a minimum magnification scale factor in accordance with an embodiment of the present invention.

FIG. 5 presents a flow chart illustrating the process of determining a minimum magnification scale factor in accordance with an embodiment of the present invention. The system starts by determining the current profile and optometric prescription for user 102 (step 502). For example, the system might determine that user 102 has selected the profile for viewing with the aid of corrective lenses, and user 102's optometric prescription for this profile calls for correcting for 20/100 vision.

Next, the system determines the magnification scale factor settings for the currently selected profile (step 504) by referencing near-vision chart 200 and analyzing the profile settings. For example, the current profile might require the magnification scale factor to be set based on the smallest font size used, as opposed to the average font size or the most used font size. In addition, because different fonts look slightly different when rendered, the system corrects for the specific fonts being used (step 506). Finally, the system takes all of these settings and configurations into account and determines the appropriate magnification scale factor (step 508).

The foregoing descriptions of embodiments of the present invention have been presented only for purposes of illustration and description. They are not intended to be exhaustive or to limit the present invention to the forms disclosed. Accordingly, many modifications and variations will be apparent to practitioners skilled in the art. Additionally, the above disclosure is not intended to limit the present invention. The scope of the present invention is defined by the appended claims.

What is claimed is:

1. A computer-implemented method, comprising:
   receiving predetermined optometric correction information for a user;
   subsequent to said receiving, adjusting a magnification scale factor for an output based on the predetermined optometric correction information and based on at least one font characteristic of the output, wherein the font characteristic includes one or more of: smallest font size in the output, average font size in the output, most frequently used font size in the document, and font type in the output, wherein the output includes textual content and graphical content, and wherein the magnification scale factor is configured to enlarge the output;
   generating a transformation matrix for the output according to the magnification scale factor;
   rendering the output with the transformation matrix to create an enlarged output, wherein the enlarged output includes enlarged textual content and enlarged graphical content; and
   displaying the enlarged output, wherein the displayed enlarged output is not used to determine the optometric correction information.

2. The method of claim 1, further comprising determining, prior to said receiving, the optometric correction information, wherein said determining the optometric correction information comprises:
   presenting an eye chart to the user;
   receiving a selection of a smallest legible line on the eye chart from the user; and
   determining the optometric correction information from the selected legible line.

3. The method of claim 1, wherein displaying the enlarged output includes:
   displaying the enlarged output on a CRT or LCD display; or
   printing the enlarged output on paper.

4. The method of claim 1, wherein the optometric correction information is specified as diopters.

5. The method of claim 1, wherein the optometric correction information is specified as a distance correlation.

6. The method of claim 1, wherein the optometric correction information is specified as a Jaeger Number.

7. The method of claim 1, wherein the optometric correction information is specified as a font point size.

8. The method of claim 1, wherein the optometric correction information is specified as a visual efficiency percentage.

9. A computer-readable storage medium storing instructions that when executed by a computer cause the computer to perform a method comprising:
   receiving predetermined optometric correction information for a user;
   subsequent to said receiving, adjusting a magnification scale factor for an output based on the predetermined optometric correction information and based on at least one font characteristic of the output, wherein the font characteristic includes one or more of: smallest font size in the output, average font size in the output, most frequently used font size in the document, and font type in the output, wherein the output includes textual content and graphical content, and wherein the magnification scale factor is configured to enlarge the output;
   generating a transformation matrix for the output according to the magnification scale factor;
   rendering the output with the transformation matrix to create an enlarged output, wherein the enlarged output includes enlarged textual content and enlarged graphical content; and
   displaying the enlarged output, wherein the displayed enlarged output is not used to determine the optometric correction information.

10. The computer-readable storage medium of claim 9, wherein the method further comprises determining, prior to said receiving, the optometric correction information, wherein said determining the optometric correction information comprises:

presenting an eye chart to the user;
 receiving a selection of a smallest legible line on the eye chart from the user; and
 determining the optometric correction information from the selected legible line.

11. The computer-readable storage medium of claim 9, wherein displaying the enlarged output includes:

displaying the enlarged output on a CRT or LCD display; or
 printing the enlarged output on paper.

12. The computer-readable storage medium of claim 9, wherein the optometric correction information is specified as diopters.

13. The computer-readable storage medium of claim 9, wherein the optometric correction information is specified as a distance correlation.

14. The computer-readable storage medium of claim 9, wherein the optometric correction information is specified as a Jaeger Number.

15. The computer-readable storage medium of claim 9, wherein the optometric correction information is specified as a font point size.

16. The computer-readable storage medium of claim 9, wherein the optometric correction information is specified as a visual efficiency percentage.

17. An apparatus, comprising:

a receiving mechanism configured to receive predetermined optometric correction information for a user;
 a magnification mechanism configured to:
  adjust a magnification scale factor for an output based on the predetermined optometric correction information and based on at least one font characteristic of the output, wherein the font characteristic includes one or more of: smallest font size in the output, average font size in the output, most frequently used font size in the document, and font type in the output, wherein the output includes textual content and graphical content, and wherein the magnification scale factor is configured to enlarge the output; and
  generate a transformation matrix for the output according to the magnification scale factor;
 a rendering mechanism configured to render the output with the transformation matrix to create an enlarged output, wherein the enlarged output includes enlarged textual content and enlarged graphical content; and
 a display mechanism configured to display the enlarged output, wherein the displayed enlarged output is not used to determine the optometric correction information.

18. The apparatus of claim 17, further comprising:

a presentation mechanism configured to present an eye chart to the user;
 wherein the apparatus is further configured to receive a selection of a smallest legible line on the eye chart from the user, to determine the optometric correction information from the selected legible line, and to provide the optometric correction information to the receiving mechanism as the predetermined optometric correction information.

19. The apparatus of claim 17, wherein the display mechanism is configured to:

display the enlarged output on a CRT or LCD display; or
 print the enlarged output on paper.

20. The apparatus of claim 17, wherein the optometric correction information is specified as diopters.

* * * * *